United States Patent [19]

Knetsch et al.

[11] 4,122,852

[45] Oct. 31, 1978

[54] DEVICE FOR APPLYING PRESSURE TO A SELECTED POINT OF A HUMAN FINGER

[76] Inventors: Wilfried Knetsch, Babenbergergasse 7/1, 2340 Mödling; Elisabeth Petricek, Anton Brucknergasse 9, 3400 Klosterneuburg, both of Austria

[21] Appl. No.: 690,029

[22] Filed: May 25, 1976

[30] Foreign Application Priority Data

May 26, 1975 [AT] Austria ................................ 4002/75

[51] Int. Cl.$^{2}$ ............................................. A61B 17/00

[52] U.S. Cl. ............................ 128/303 R; 128/329 A

[58] Field of Search ................... 24/20 S, 23 R, 16 R; 128/329 R, 329 A, 303 R

[56] References Cited

U.S. PATENT DOCUMENTS

| | | | |
|---|---|---|---|
| 2,423,627 | 7/1947 | Tinnerman | 24/23 R X |
| 3,749,099 | 7/1973 | Cotey | 128/329 X |
| 3,923,064 | 12/1975 | Leupold | 128/329 A |

FOREIGN PATENT DOCUMENTS

| | | | |
|---|---|---|---|
| 811,968 | 1/1937 | France | 24/20 S |

*Primary Examiner*—Robert W. Michell
*Assistant Examiner*—Michael H. Thaler
*Attorney, Agent, or Firm*—McGlew & Tuttle

[57] ABSTRACT

A device for applying pressure to a selected point on the human finger comprising an open clamping ring having crossing end portions which extend beyond the circumference of the ring, at least one actuating projection on the circumference of the ring extending radially outwardly therefrom and pressure means axially aligned with the actuating means and extending inwardly therefrom beyond the inner surface of the ring.

7 Claims, 5 Drawing Figures

DEVICE FOR APPLYING PRESSURE TO A SELECTED POINT OF A HUMAN FINGER

FIELD OF THE INVENTION

Figure 1:
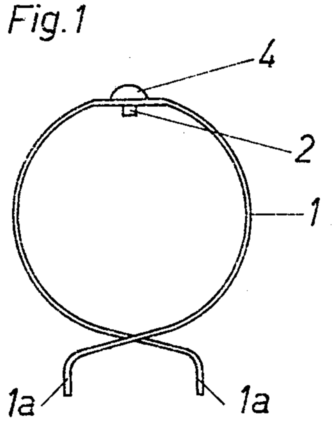

This invention relates in general to devices for applying pressure to selected locations on the human body for therapeutic reasons and in particular to a device for applying pressure to a selected point on the human finger to accomplish treatments of acupuncture or acupressure.

DESCRIPTION OF THE PRIOR ART

Acupuncture is a medical treatment in which metal needles are driven into the human body in certain areas of the skin, referred to as organ segments, or at exactly defined points, so that pain in diseased organs or parts of the body which are associated with certain skin areas or points is alleviated or diminished and analgesy can thus be effected. A modification of this treatment is known as acupressure, in which a slender pin is used to apply pressure, which may be relatively strong, on the defined points of the skin, either by massage or by an engagement of the pin with the skin at a fixed point. In his book "Massage in Chinese Medicine", published by Edition Maisonnuve, Paris 1971, J, Borsarello has taught on page 111 to use a rod which is about 5–6 mm in diameter and has a spherical end for a gentle massage of the so-called cardinal point.

The Chinese science of acupuncture as described, e.g., by Huamn Ti Nei Ching in "Textbook of Acupuncture", published by Guozi Shudian, Peking, defines at the distal digit of each forefinger on the side facing the thumb a point which is described a TING point or as point Dil. This point is laterally spaced about 1 to 2 mm from the nail bed, specifically from the outer angle of the nail groove. When these two TING points are sumultaneously subjected to acupuncture or acupressure, the jaw region which is associated in the nervous system with these two TING points, and the mouth cavity, can be temporarily relieved from pain.

For use during dental treatment, a device for subjecting the Dil point at the distal digit of the forefinger to acupressure has already been developed. That device consists essentially of a holder, which has the shape of a closed or split ring and is adapted to be slipped on the thumb. This ring is provided on its outer surface with a pressure plate, which extends transversely to the plane defined by the ring, and with a short spherical projection approximately at the center of the pressure plate. For acupressure by means of such devices, an annular holder is fitted on each thumb of the patient so that the projection is directed toward the adjacent forefinger and the patient then engages each projection as exactly as possible with said Dil point and forces the projection against said point from the outside. That method is unsatisfactory, however, because the engagement of the projection exactly with the Dil point is not ensured, this exact engagement being essential, and a substantially constant pressure throughout the treatment is also not realized, such treatment often taking a relatively long time.

SUMMARY OF THE INVENTION

The invention relates to an acupressure device which may be used to apply pressure to a selected point on a human finger and which eliminates the aforementioned disadvantages in a simple and satisfactory manner. The device comprises an open clamping ring which is made of resilient material and which is preferably provided at both ends with handles, extending substantially radially outwardly. These handle portions cross each other. At a location substantially opposite the handle crossing the clamping ring has an apex portion. At this apex portion there is a radially inwardly directed pressure pin attached. The resilient clamping ring is adapted to be fitted on a finger which is to be treated, e.g., a forefinger, and the pressure pin on the inside of the clamping ring is adapted to be forced against a selected point of the finger by pressure applied to the outside of the clamping ring.

According to a preferred feature of the invention, a centering cup which is slightly concave is attached to the inside of the apex portion of the resilient clamping ring and the pressure pin is attached to said centering cup and protrudes therefrom. According to a further preferred feature, the pressure pin and the concave centering cup may be offset from the middle of said apex portion.

According to a further preferred feature of the invention, the resilient clamping ring is provided on its outer surface with a substantially cylindrical projection. This projection is coaxial with the pressure pin and preferably larger in diameter than the pressure pin. It is engageable by a finger, e.g., by the thumb, for actuating the device.

An object of the invention is to provide a device for accurately locating and applying a substantially constant pressure to points on fingers and related extremities in acupressure or acupuncture treatments.

A further object of this invention is to provide a device which is rugged in construction, simple in design and economical to manufacture.

BRIEF DESCRIPTION OF THE PREFERRED EMBODIMENT

Figure 1A:
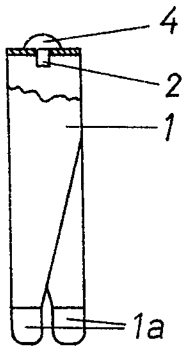
Figure 2:
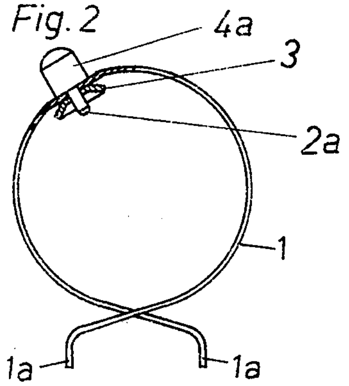
Figure 3:
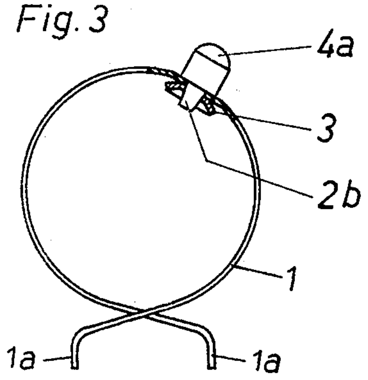
Figure 4:
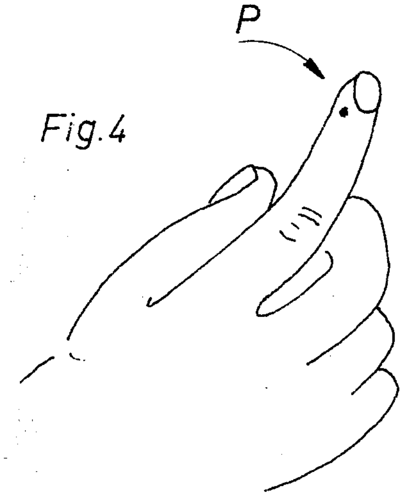

FIG. 1 is an elevational view of the invention,

FIG. 1*a* is a partly in section side view of the clamping ring in FIG. 1, FIG. 2 is a partly in section elevation of another embodiment of the invention, FIG. 3 is a partly in section elevation of another embodiment of the invention, FIG. 4 is a perspective view of a human hand showing the TING or Dil point on the index finger.

GENERAL DESCRIPTION OF THE PREFERRED EMBODIMENT

Refering to the drawing in particular the invention embodied therein comprises a split clamping ring 1, as shown in FIG. 1 and 1*a* which consists of a resilient metal strip and is provided with two outwardly projecting handle portions 1*a*, which cross each other. The clamping ring 1 has an apex portion. A radially inwardly directed pressure pin is attached to said apex portion on the inside thereof. An actuating projection 4, which is larger in diameter than the pressure pin 2 and coaxial thereto, is attached to the outside of the apex portion.

FIGS. 2 and 3 show particularly preferred embodiments of the acupressure device. A centering cup 3 which is slightly concave inwardly is attached to the resilient clamping ring 1 on the inside thereof and the pressure pin 2*a* or 2*b* is attached to said cup and slightly protrudes therefrom. The centering cup 3 as well as the cylindrical actuating projection 4*a*, which is coaxial to the centering cup 3, are offset from the center of the peripheral extent of the apex portion of the ring. The clamping ring 1 shown in FIG. 2 has a pressure pin *2a*, which has a hemispherical free end. The pressure pin *2b* shown in FIG. 3 has a slender end portion in the form of a truncated cone.

The acupressure device designed in accordance with the invention may be used, during dental treatments, as follows: Shortly before the beginning of the dental treatment, a resilient clamping ring 1 is fitted on the distal digit of each forefinger 1 in such a manner that the pressure pin 2 or *2a* or *2b* engage exactly over the TING point which is disposed on the outside of the forefinger and indicated at P in FIG. 4. Throughout the dental treatment, the patient applies pressure with his thumbs from the outside on the actuating projection 4 or *4a* provided on each clamping ring 1 so that an appreciable, intense pressure is applied by the pressure pin 2 or *2a* or *2b* to the TING point. Because the clamping ring 1 is fitted on the forefinger to which pressure is to be applied, the pressure pin 2 or *2a* or *2b* will immovably remain in engagement with the TING point P so that the continued application of the required pressure is ensured. When this device is used in the prescribed manner, pain in the region of the jaws and the entire mouth cavity is greatly diminished or even completely alleviated.

While specific embodiments of the invention have been shown and described in detail to illustrate the application of the principles of the invention, it will be understood that the invention may be embodied otherwise without departing from such principles.

What we claim is:

1. A device for applying pressure to a selected point on the human finger comprising a split resilient clamping ring engageable over the finger with inner and outer circumferential surfaces and having end portion which cross each other at a point on the circumference of said ring and which extend radially outwardy from said outer circumferential surface, an actuating projection on said ring extending radially outwardly from said outer circumferential surface, pressure means connected to said actuating projection and extending radially inwardly therefrom and radially inwardly of said inner circumferential surface, and including a centering cup in the form of a dish which is concave radially inwardly toward the center of said ring, surrounding said pressure means on the inner circumference of said ring.

2. A device according to claim 1 wherein said pressure means is pin-shaped for puncturing the skin of said finger.

3. A device according to claim 1 wherein said pressure means is a truncated cone tapering inwardly for applying pressure to the surface of said finger.

4. A device according to claim 1, wherein said actuating projection is cylindrical and adapted to be pressed from outside said ring in order to apply pressure to the finger through the pressure means.

5. A device according to claim 1 wherein said ring end portions have a bend therein extending outwardly from the outer of said ring to form ring expanding handles to open said ring and allow the insertion of said finger.

6. A device according to claim 1 wherein said actuating projection is directly opposite said end portion crossing on said ring circumference.

7. A device according to claim 1 wherein said actuating projection is off-set from a position opposed to said end portion crossing on said circumference.

* * * * *